United States Patent
Yuasa et al.

(10) Patent No.: US 9,757,357 B2
(45) Date of Patent: Sep. 12, 2017

(54) PHOTODYNAMIC THERAPY OR DIAGNOSTIC AGENT, USING INFRARED-SPECTRUM LIGHT

(75) Inventors: Hideya Yuasa, Tokyo (JP); Shun-ichiro Ogura, Tokyo (JP); Kiwamu Takahashi, Tokyo (JP); Katushi Inoue, Tokyo (JP); Tohru Tanaka, Tokyo (JP)

(73) Assignees: Tokyo Institute of Technology, Tokyo (JP); SBI Pharmaceuticals Co., Ltd., Tokyo (JP)

( * ) Notice: Subject to any disclaimer, the term of this patent is extended or adjusted under 35 U.S.C. 154(b) by 56 days.

(21) Appl. No.: 14/113,877

(22) PCT Filed: Apr. 27, 2012

(86) PCT No.: PCT/JP2012/002939
§ 371 (c)(1),
(2), (4) Date: Oct. 25, 2013

(87) PCT Pub. No.: WO2012/153493
PCT Pub. Date: Nov. 15, 2012

(65) Prior Publication Data
US 2014/0056817 A1    Feb. 27, 2014

(30) Foreign Application Priority Data

May 6, 2011    (JP) .................................. 2011-103816

(51) Int. Cl.
| A61K 31/409 | (2006.01) |
| A61K 41/00 | (2006.01) |
| A61K 49/00 | (2006.01) |
| A61K 31/197 | (2006.01) |

(52) U.S. Cl.
CPC .......... *A61K 31/409* (2013.01); *A61K 31/197* (2013.01); *A61K 41/0061* (2013.01); *A61K 41/0071* (2013.01); *A61K 49/0019* (2013.01); *A61K 49/0021* (2013.01); *A61K 49/0052* (2013.01); *A61K 49/0093* (2013.01)

(58) Field of Classification Search
CPC ............ A61K 41/0061; A61K 41/0071; A61K 49/0093; A61K 49/0052; A61K 31/409; A61K 49/0021; A61K 49/0019; A61K 31/197
USPC .................................. 424/9.6; 514/422, 561
See application file for complete search history.

(56) References Cited

U.S. PATENT DOCUMENTS

| 2008/0020029 A1 | 1/2008 | Kojima et al. |
| 2011/0022129 A1* | 1/2011 | Prud'homme ....... A61K 9/0009 607/88 |
| 2011/0112059 A1* | 5/2011 | Hasan et al. .................. 514/209 |
| 2011/0123439 A1* | 5/2011 | Cheon ................ A61K 49/0002 424/1.37 |

FOREIGN PATENT DOCUMENTS

| JP | 02-264651 A | 10/1990 |
| JP | 2007-186580 A | 7/2007 |
| JP | 2009-024115 A | 2/2009 |
| JP | 2010-53079 | * 3/2010 |
| WO | WO 2005/087196 A1 | 9/2005 |

OTHER PUBLICATIONS

Ikehara et al., "Cancer vaccine delivery system using oligomannose coated liposome (OML)," Proceedings of the Japanese Cancer Association, Aug. 28, 2006, 65:444, with English translation.
Kaneko, Sadao, "A Current Overview: Photodynamic Diagnosis and Photodynamic Therapy using 5-Aminolevulinic Acid in Neurosurgery," JJSLSM, 2008, 29(2):135-146 (in English).
Kobayashi et al., "Development of sugar-lanthanide upconversion nanoparticles for the imaging of lectins," CSJ: The Chemical Society of Japan Koen Yokoshu, 2010, 90(3):769, 1D4-46, English abstract.
Matsui et al., "Targeted delivery of oligomannose-coated liposome to the omental micrometastatis by peritoneal macrophages from patients," Proceedings of the Japanese Cancer Association, Aug. 31, 2009, 68:51, English abstract.
Tanaka et al., "Development status of ALA-PDD, PDT in the world, and enlargement of the application field," JJSLSM, 2009, 30(2):198, with English translation.
Tanaka, Toru, "Actual status and future of PDD, PDT using 5-aminolevulinic acid," The Japanese Journal of Urology, Feb. 20, 2010, 101(2):133, with English translation.

(Continued)

*Primary Examiner* — Johann R Richter
*Assistant Examiner* — Robert Cabral
(74) *Attorney, Agent, or Firm* — Foley & Lardner LLP

(57) ABSTRACT

It is intended to provide a therapeutic and/or diagnostic agent that can be used in photodynamic therapy (PDT) or photodynamic diagnosis (PDD) capable of utilizing infrared-spectrum light such as near-infrared light (NIR), infrared light, or far-infrared light, which attains a deep body penetration. The present invention provides a photodynamic therapeutic or diagnostic agent or a photodynamic therapeutic or diagnostic kit for cancer or infectious disease, comprising: a particle (e.g., a lanthanide particle) that emits upconversion luminescence by infrared-spectrum light such as near-infrared light having a wavelength of 0.7 µm to 2.5 µm; and a photosensitizer (e.g., porphyrin) or a 5-aminolevulinic acid group.

7 Claims, 4 Drawing Sheets

(56) References Cited

OTHER PUBLICATIONS

Yuasa et al., "Near-Infrared Photodynamic Therapy Using Suger-Lanthanide Nanoparticles and 5-Aminolevurinic Acid," The Japanese Society of Carbohydrate Research Nenkai Yoshishu, Jun. 27, 2011, 118:P-092, English summary.
Zhang et al., "Versatile Photosensitizers for Photodynamic Therapy at Infrared Excitation," J. Am. Chem. Soc., Apr. 18, 2007, 129(15):4526-4527.
Chatterjee et al., "Nanoparticles in photodynamic therapy: An emerging paradigm," Advanced Drug Delivery Reviews, Dec. 14, 2008, 60(15):1627-1637.
Chatterjee et al., "Upconversion fluorescence imaging of cells and small animals using lanthanide doped nanocrystals," Biomaterials, Dec. 3, 2007, 29(7):937-943.
Guo et al., "Singlet oxygen-induced apoptosis of cancer cells using upconversion fluorescent nanoparticles as a carrier of photosensitizer," Nanomedicine: Nanotechnology, Biology and Medicine, Jun. 1, 2010, 6(3):486-495.
Mader et al., "Upconverting luminescent nanoparticles for use in bioconjugation and bioimaging," Current Opinion in Chemical Biology, Oct. 1, 2010, 14(5):582-596.

\* cited by examiner

Figure 1]
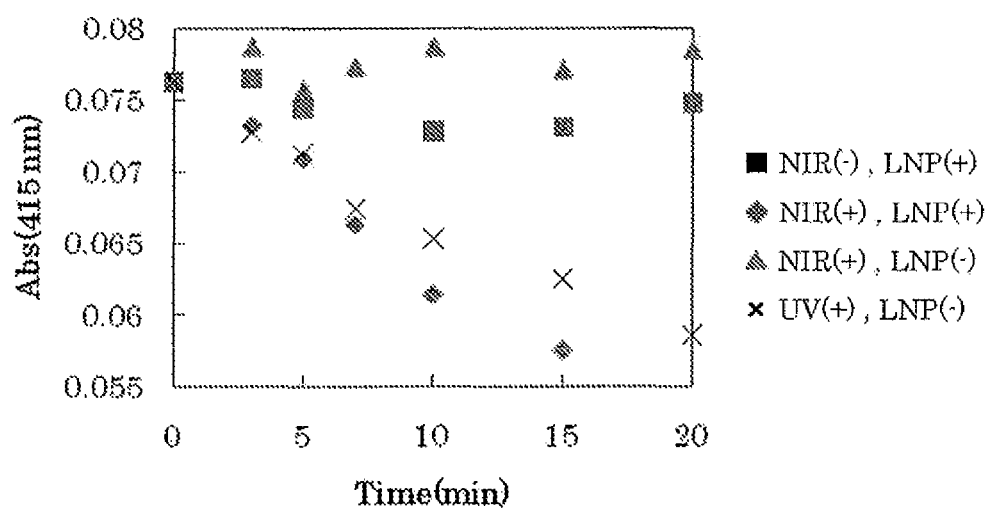
Figure 2
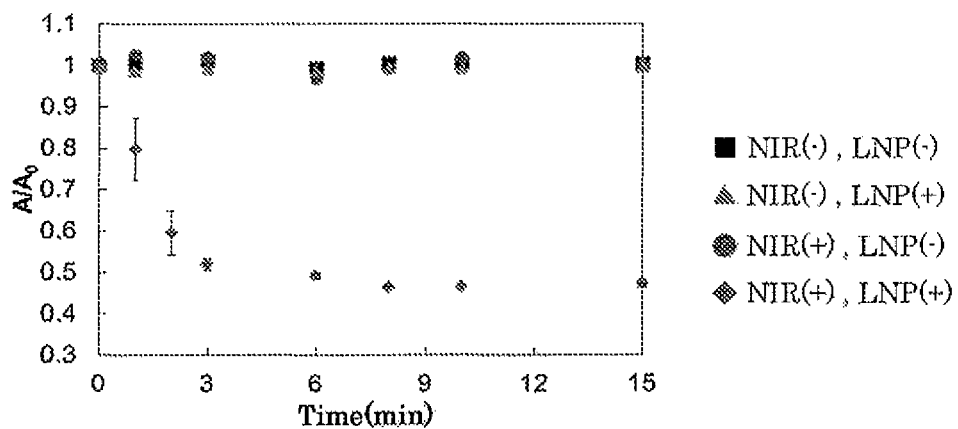

Figure 3
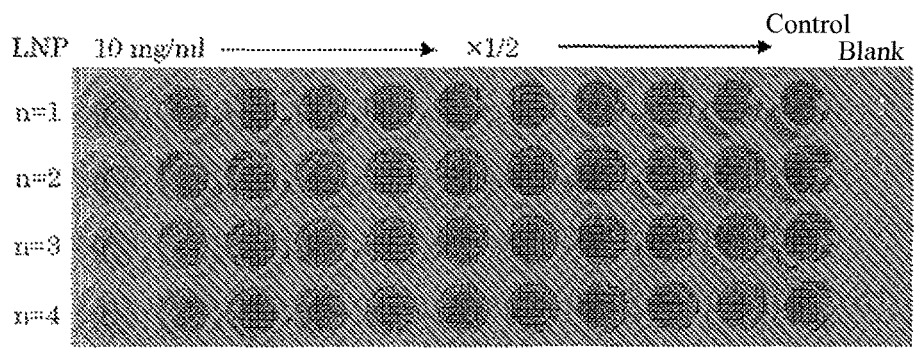
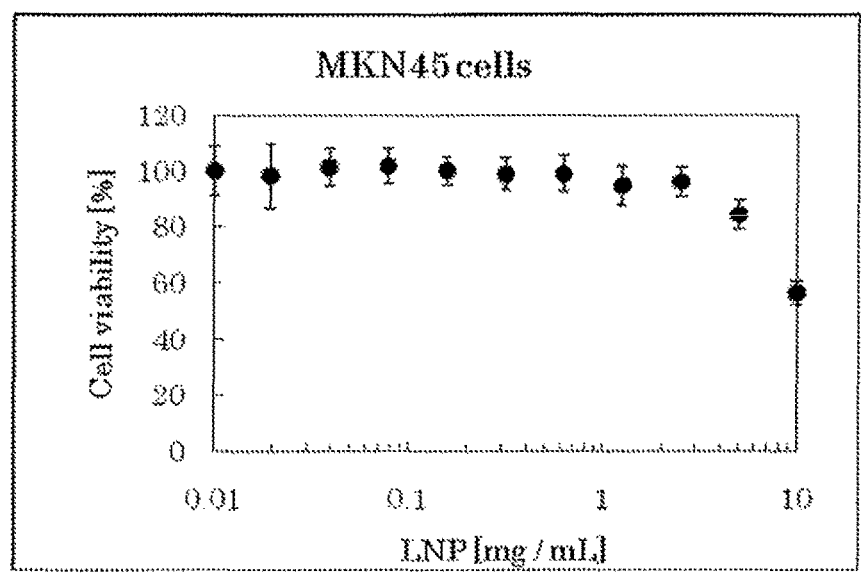
Figure 4
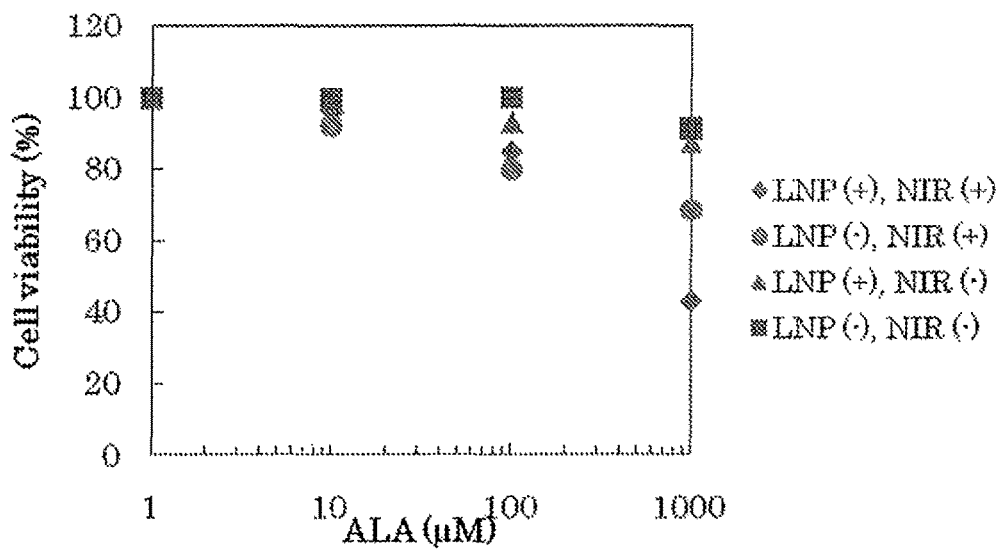

PHOTODYNAMIC THERAPY OR DIAGNOSTIC AGENT, USING INFRARED-SPECTRUM LIGHT

CROSS-REFERENCE TO RELATED APPLICATIONS

This application is a National Stage application of PCT/JP2012/002939, filed Apr. 27, 2012, which claims priority from Japanese application no. JP 2011-103816, filed May 6, 2011.

TECHNICAL FIELD

The present invention relates to a photodynamic therapeutic or diagnostic agent based on infrared-spectrum light. Specifically, the present invention relates to a photodynamic therapeutic or diagnostic agent comprising: a particle (e.g., a lanthanide particle) in which upconversion of infrared-spectrum light can take place; and a photosensitizer or a 5-aminolevulinic acid or a derivative thereof, or a salt of the 5-aminolevulinic acid or the derivative (hereinafter referred to as "a 5-aminolevulinic acid group").

BACKGROUND ART

In vivo imaging techniques are now essential in medical settings. An exemplary method involves administering 5-aminolevulinic acid (ALA) to a cancer patient and detecting the red emission of its metabolite protoporphyrin IX (PPIX) by blue light excitation to confirm the outline of ill-defined tumor. This method is used in order to assist surgical operation.

Such a method for locally diagnosing tumor by use of fluorescence generated by a light-sensitive substance accumulated in tumor is called photodynamic diagnosis (PDD). Upon excitation, PPIX further generates active oxygen called singlet oxygen, which can in turn destroy cancer tissues. The blue light excitation, however, merely causes the destruction of cancer tissues located in the surface due to its low tissue penetration. Accordingly, use of excitation light having higher tissue penetration can be expected to produce therapeutic effects. Use of near-infrared light (NIR) can overcome not only low tissue penetration but the problems of background fluorescence from excitation in ultraviolet to visible light regions and phototoxicity. Lanthanide nanoparticles (LNP) are known as a tool that achieves this NIR excitation having various advantages (see for example, patent document 1). Usual fluorescent groups emit light with lower energy than that of excitation light, whereas LNP emits, by NIR excitation, visible light with higher energy. This upconversion luminescence is receiving attention.

For example, an antibody-LNP complex having a cancer antigen-specific antibody bonded to the surface of a silica layer doped with the photosensitizing dye merocyanine 540 and coated on LNP (NaYF$_4$; Yb$^{3+}$,Er$^{3+}$) (see for example, non-patent document 1) and a fine phosphor particle-organic dye complex in which a porphyrin dye having a terminal carboxyl group is bonded via an amide bond to the surface of a rare-earth element-containing fine phosphor particle that emits upconversion luminescence, wherein the complex attains a deep body penetration and is suitable for a photodynamic therapy method, etc. (see for example, patent document 2) have been proposed as photodynamic therapy (PDT) using such upconversion luminescence.

PRIOR ART DOCUMENTS

Patent Documents

Patent Document 1: Japanese unexamined Patent Application Publication No. 2007-186580
Patent Document 2: Japanese unexamined Patent Application Publication No. 2009-24115

Non-Patent Documents

Non-patent Document 1: J. AM. CHEM. SOC. 2007, 129, 4526-4527

SUMMARY OF THE INVENTION

Object to be Solved by the Invention

PDT involves irradiating a lesion with light after administration of a sensitizer and removing, for example, infectious bacteria or cancer cells by use of the killing effects of generated active oxygen, various radicals, or the like. This technique is low invasive and scarless compared with a general method such as surgery and is therefore receiving attention as a next-generation therapy method. Its range of application, however, has been limited to skin disease, etc., because this technique is merely applicable to a depth that can be reached by light for exciting the sensitizer. Although sensitizers excitable by long-wavelength light that reaches as deeply as possible have been developed, the excitation light has a wavelength of 664 nm even for Laserphyrin, which can be excited by the longest wavelength, and thus reaches insufficiently deeply.

PDD involves irradiating a lesion with excitation light after administration of a sensitizer and observing fluorescence emitted by the sensitizer to perform diagnosis. This approach, however, tends to cause false negative because excitation light suitable for many sensitizers has a wavelength around 400 nm and is blocked by fat, etc.

An object of the present invention is to provide a therapeutic and/or diagnostic agent that can be used in PDT or PDD capable of utilizing infrared-spectrum light such as near-infrared light (NIR), infrared light, or far-infrared light, which attains a deep body penetration.

Means to Solve the Object

The present inventors have found that PDT or PDD using infrared-spectrum light that attains a deep body penetration can be achieved by the combined use of a 5-aminolevulinic acid group and LNP. On the basis of this finding, the present invention has been completed.

Specifically, the present invention relates to: (1) a photodynamic therapeutic or diagnostic agent comprising: a particle that emits upconversion luminescence by infrared-spectrum light; and a photosensitizer or a 5-aminolevulinic acid group; (2) the photodynamic therapeutic or diagnostic agent according to (1), wherein the particle that emits upconversion luminescence by infrared-spectrum light is a lanthanide particle; (3) the photodynamic therapeutic or diagnostic agent according to (2), wherein the lanthanide particle is a complex with mannose; (4) the photodynamic therapeutic or diagnostic agent according to any one of (1) to (3), wherein the photosensitizer is a tetrapyrrole compound; (5) the photodynamic therapeutic or diagnostic agent according to any one of (1) to (3), wherein the 5-aminolevulinic acid group is 5-aminolevulinic acid or a derivative thereof, or a salt of the 5-aminolevulinic acid or the derivative; (6) the photodynamic therapeutic or diagnostic agent according to any one of (1) to (5), wherein the infrared-spectrum light is near-infrared light having a wavelength of 0.7 μm to 2.5 μm; and (7) the photodynamic therapeutic or diagnostic agent according to any one of (1) to (6), wherein the photodynamic therapeutic or diagnostic agent is a therapeutic or diagnostic for cancer.

Effect of the Invention

The present invention can achieve PDT or PDD using infrared-spectrum light that attains a deep body penetration. Thus, the present invention can expand the target of PDT or PDD, which has previously been limited to lesions located in surface layers, to lesions throughout the body.

BRIEF DESCRIPTION OF DRAWINGS

FIG. 1 is a diagram showing results of an experiment on the generation of singlet oxygen from protoporphyrin IX by the emission of commercially available lanthanide particles.

FIG. 2 is a diagram showing results of an experiment on the generation of singlet oxygen from protoporphyrin IX by the emission of commercially available lanthanide particles in another aspect.

FIG. 3 is a diagram showing results of a test on the cytotoxicity of commercially available lanthanide particles.

FIG. 4 is a diagram showing results of an experiment on cancer cell injury by the emission of commercially available lanthanide particles and protoporphyrin IX.

MODE OF CARRYING OUT THE INVENTION

Figure 5:
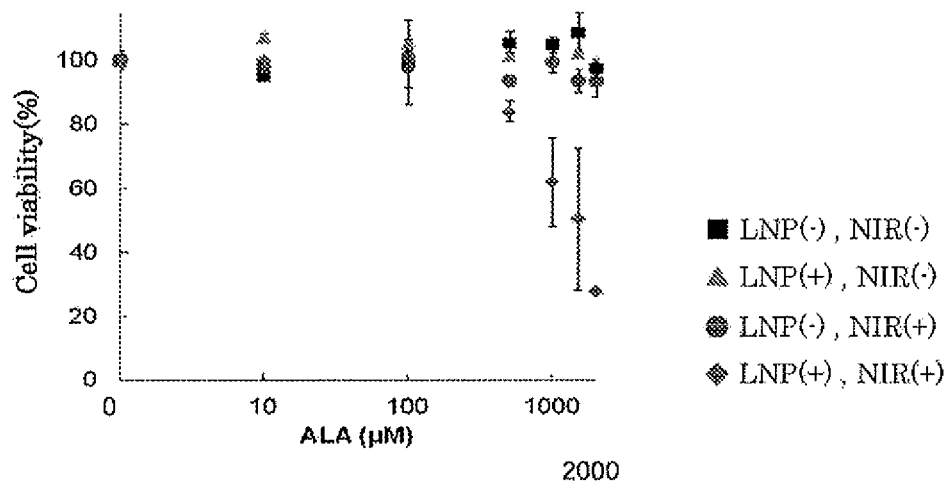
FIG. 5 is a diagram showing results of an experiment on cancer cell injury by the emission of commercially available lanthanide particles and protoporphyrin IX in another aspect.

The photodynamic therapeutic or diagnostic agent of the present invention is not particularly limited as long as the agent comprises: a particle that emits upconversion luminescence by infrared-spectrum light; and a photosensitizer or a 5-aminolevulinic acid group. The photodynamic therapeutic or diagnostic agent of the present invention can be combined with an infrared-spectrum light irradiation device to thereby achieve the PDT or PDD of cancer, dysplasia, bacterium- or fungus-infected sites, and virus-infected cells as well as affected areas such as inflammatory sites attributed to allergy. Also, the photodynamic therapeutic or diagnostic agent of the present invention can be provided as a photodynamic therapeutic or diagnostic kit.

In the present invention, the infrared-spectrum light refers to light that has high body permeability and belongs to the wavelength regions of approximately 0.7 μm to 1 mm. Such infrared-spectrum light is classified into: near-infrared light having a wavelength of 0.7 μm to 2.5 μm; mid-infrared light having a wavelength of 2.5 μm to 4 μm; and far-infrared light having a wavelength of 4 μm to 1 mm. Among these infrared-spectrum lights, near-infrared light having relatively high energy and high body permeability, more preferably near-infrared light having a wavelength of 0.7 μm to 1.5 μm, can be used advantageously. These infrared-spectrum lights are usually supplied from a lamp or a laser beam. However, the light source is not particularly limited as long as the light source can supply light in these wavelength ranges.

In the present invention, the upconversion is one kind of anti-Stokes shift and refers to a quantum phenomenon in which, under additional photons, atoms or molecules in an excited state emit short-wavelength light with higher energy than that of the initially irradiated light. The upconversion luminescence refers to light that is generated from a substance that emits upconversion luminescence upon light irradiation and has higher energy than that of the excitation energy (i.e., light having a shorter wavelength than that of the excitation light).

Preferred examples of the particle that emits upconversion luminescence by infrared-spectrum light (hereinafter, also referred to as an "upconversion particle") can include particles comprising a plurality of lanthanoid ions, preferably fine particles having an average particle size of 10 to 500 nm, more preferably 50 to 200 nm. Examples of the lanthanoid elements can include 15 elements of atomic numbers 57 to 71, i.e., La, Ce, Pr, Nd, Pm, Sm, Eu, Gd, Tb, Dy, Ho, Er, Tm, Yb, and Lu. Among these lanthanoid ions, examples of those having high upconversion efficiency can include complexes of $Yb^{3+}$ (ytterbium ion) with $Er^{3+}$ (erbium ion), $Ho^{3+}$ (holmium ion), or $Tm^{3+}$ (thulium ion). In the case of particles comprising $Yb^{3+}$ and $Er^{3+}$, $Yb^{3+}$ absorbs the energy of infrared-spectrum light through f-orbital transition and transfers, through nonradiative transition, this energy to $Er^{3+}$, which in turn causes transition similar to multiphoton absorption to emit visible light with higher energy per unit than that of the irradiated light. Such lanthanoid particles are well known. For example, $NaYF_4$; Yb/Er absorbs 980-nm near-infrared light and emits visible light around 650 nm and 550 nm, while $NaYF_4$; Yb/Tm absorbs 980-nm near-infrared light and emits 800-nm near-infrared light and 460-nm visible light.

These lanthanoid particles are commercially available for screening, and such commercially available products may be purchased for use. Alternatively, synthetic products prepared on the basis of a method known in the art may be used. The lanthanoid particles, for example, $NaYF_4$; Yb/Er, can be synthesized by mixing $YbCl_2.6H_2O$, $YbCl_3.6H_2O$, $ErCl_3.6H_2O$, $NH_4F$, NaCl, polyethyleneimine, and ethylene glycol and heating the mixture to approximately 200° C. in an autoclave. Lanthanoid particles having various particle sizes or different upconversion characteristics can be synthesized by the fine adjustment of compositional ratios, heating temperatures, and/or heating times.

The lanthanoid particles thus synthesized may be used directly or may be pulverized into a nano size and used as lanthanoid nanoparticles (LNP). Also, the particles may be surface-modified according to a standard method. Such surface modification, for example, with a sugar or an amino acid, can improve in vivo compatibility or can control cellular uptake.

For example, macrophages, which phagocytize cancer tissues, have mannose receptors, β-glucan receptors, Fc receptors, and the like and can be imaged specifically using a probe, for example, a mannose-LNP complex comprising 1-aminoethylmannose (NEtMan) added to LNP. Since cancer tissues or tumor tissues exhibit significantly enhanced vascular permeability compared with normal tissues, fine particles easily extravasate into these tissues through blood vessels. In addition, the cancer tissues or the tumor tissues have the property of causing the accumulation of the fine particles that have reached these tissues, due to the immature lymphatic system. The passive targeting of cancer cells can be achieved by use of such enhanced permeation and retention (EPR) effects. Furthermore, LNP having a particle size adjusted to 50 nm to 200 nm, when administered to a blood vessel, can selectively arrive at tissues having high vascular permeability, i.e., cancer tissues or tumor tissues, and accumulate in these tissues.

In the present invention, the administration of the lanthanoid particles is not particularly limited by its method as long as the method is capable of administering the particles to a site targeted by PDT or PDD. Examples of the administration method can include direct injection approaches using injection as well as administration methods such as intravenous injection, drip infusion, intraarterial injection, patch, transnasal administration, intravesical injection, enema, and sublingual administration. Table 1 shows the emission of various lanthanoid particles. In this table, PEI in the column "Coating agent" means polyethyleneimine.

active oxygen by light irradiation, the compound is metabolized in vivo after administration into a photosensitizing substance protoporphyrin that acts advantageously as a photosensitizer. In the case of administering the ALAs, the accumulation of protoporphyrin IX is specific for affected areas such as cancer, dysplasia, bacterium- or fungus-infected sites, or virus-infected cells. Also, ALAs are highly safe compounds and therefore act as the most promising photosensitizer.

Each ALA derivative can be represented by the formula $R^2R^1NCH_2COCH_2CH_2COR^3$ [wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group, provided that ALA wherein each of $R^1$ and $R^2$ is a hydrogen atom and $R^3$ is a hydroxy group is excluded]. Examples of the ALA derivative can include ALA methyl ester, ALA ethyl ester, ALA propyl ester, ALA butyl ester, ALA pentyl ester, and ALA hexyl ester. Preferred examples of the ALA

TABLE 1

| | Composition of lanthanide | | | | | Emission wavelength (nm) | | | Detector |
|---|---|---|---|---|---|---|---|---|---|
| | Yb | Er | Ln | Solvent | Coating agent | Annealing | 405 | 550 | 650 | Slit width |
| 1 | Bulk lanthanide particle | | | — | — | — | 1000+ | 1000+ | 1000+ | 10 |
| 2 | Bulk lanthanide particle | | | — | — | — | 18 | 1000+ | 280 | 5 |
| 3 | 18 | 2 | — | H₂O, EtOH | PEI | — | — | 196 | 251 | 10 |
| 4 | 18 | 2 | — | H₂O, EtOH | PEI | 500° C., 2 h | — | 2 | 204 | 10 |
| 5 | 18 | 2 | Tb: 1 | H₂O, EtOH | PEI | — | — | 194 | 41 | 10 |
| 6 | 18 | 2 | Tb: 1 | H₂O, EtOH | PEI | 500° C., 2 h | — | 24 | 42 | 10 |
| 7 | 18 | — | Ho/Tb: 2/1 | H₂O, EtOH | PEI | — | — | 295 | — | 10 |
| 8 | 18 | — | Ho/Tb: 2/1 | H₂O, EtOH | PEI | 500° C., 2 h | — | 3 | — | 10 |
| 9 | 18 | 2 | Tb: 1 | Ethylene glycol | PEI | — | — | — | 2 | 10 |
| 10 | 18 | 2 | Tb: 1 | Ethylene glycol | PEI | 500° C., 2 h | — | 1 | 3 | 10 |
| 11 | 18 | 2 | In: 1 | Ethylene glycol | PEI | — | — | — | 5 | 10 |
| 12 | 18 | 2 | In: 1 | Ethylene glycol | PEI | 500° C., 2 h | — | 220 | 1000+ | 10 |
| 13 | 18 | — | Ho: 2 | Ethylene glycol | PEI | — | — | — | 1 | 10 |
| 14 | 18 | — | Ho: 2 | Ethylene glycol | PEI | 500° C., 2 h | — | 28 | 3 | 10 |
| 15 | 18 | — | Ho/Tb: 2/1 | Ethylene glycol | PEI | — | — | — | 1 | 10 |
| 16 | 18 | — | Ho/Tb: 2/1 | Ethylene glycol | PEI | 500° C., 2 h | — | 1000+ | 122 | 10 |
| 17 | 18 | 2 | — | H₂O | Boric acid | — | — | 36 | 51 | 10 |
| 18 | 18 | 2 | — | H₂O | Boric acid | 500° C., 2 h | 53 | 346 | 1000+ | 10 |

The photosensitizer according to the present invention can absorb visible light to thereby emit fluorescence and generate active oxygen. Any photosensitizer that is used in PDT or PDD can be used as the photosensitizer of the present invention. Among others, preferred examples of the photosensitizer can include tetrapyrrole compounds and can specifically include Photofrin, Laserphyrin, protoporphyrin IX, Foscan, chlorine, uroporphyrin I, uroporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, coproporphyrin I, coproporphyrin III, isocoproporphyrin, harderoporphyrin, isoharderoporphyrin, hematoporphyrin, mesoporphyrin, etioporphyrin, pyroporphyrin, deuteroporphyrin IX, pemptoporphyrin, and ATXs-10. The dose of the photosensitizer is the same as that recommended for PDT using visible light.

Examples of a 5-aminolevulinic acid group (ALAs) according to the present invention can include 5-aminolevulinic acid (ALA) and derivatives thereof, and salts of the 5-aminolevulinic acid or the derivatives. The ALA is a compound known in the art. Although the ALA itself weakly absorbs visible light and generates neither fluorescence nor derivative can include ALA derivatives having ester and acyl groups. Examples of the ALA derivatives having ester and acyl groups can specifically include ALA derivatives having the combination of a methyl ester group and a formyl group, a methyl ester group and an acetyl group, a methyl ester group and a n-propanoyl group, a methyl ester group and a n-butanoyl group, an ethyl ester group and a formyl group, an ethyl ester group and an acetyl group, an ethyl ester group and a n-propanoyl group, or an ethyl ester group and a n-butanoyl group.

The salts of the ALA or the derivatives thereof are not particularly limited and are preferably pharmaceutically acceptable acid (inorganic or organic acid)-addition salts. Examples of the inorganic acid-addition salts can include hydrochloride, hydrobromide, hydroiodide, phosphate, nitrate, and sulfate. Examples of the organic acid-addition salts can include acetate, propionate, toluenesulfonate, succinate, oxalate, lactate, tartrate, glycolate, methanesulfonate, butyrate, valerate, citrate, fumarate, maleate, and malate. Other examples of the salts can include: metal salts such as sodium salt, potassium salt, and calcium salt; ammonium salts; and alkylammonium salts. These salts are used as solutions.

Among these ALAs, ALA, ALA methyl ester, ALA ethyl ester, ALA propyl ester, ALA butyl ester, ALA pentyl ester, and hydrochlorides, phosphates, or sulfates thereof are most desirable.

These ALAs may form hydrates or solvates and can be used alone or in appropriate combination of two or more thereof. Further, ALAs can be produced by any method including chemical synthesis, microbial production, and enzymatic production.

When preparing ALAs as an aqueous solution, attention should be paid not to make the aqueous solution alkaline in order to prevent the decomposition of the ALAs. In the case where the solution gets alkaline, the decomposition of ALA can be prevented by the removal of oxygen.

The photosensitizer or the ALAs according to the present invention can be supplemented, if necessary, with other ingredients such as active ingredients, nutrients, and excipients. Examples of the dosage form of the sensitizer according to the present invention can include injections, drips, intravesical injections, tablets, capsules, fine granules, syrups, patches, and suppositories. These dosage forms can be formulated according to a routine method appropriately using solvents, dispersion media, expanders, excipients, and the like.

The photosensitizer or the ALAs according to the present invention may be administered simultaneously with the upconversion particle or may be administered separately from the upconversion particle. A pharmaceutically acceptable organic or inorganic and, usually inert, carrier material that is in a solid or liquid state and is suitable for ingestion is used as a carrier that can be mixed with the sensitizer. Specifically, examples of the carrier include crystalline cellulose, gelatin, lactose, starch, magnesium stearate, talc, plant- and animal-derived fats and oils, gum, and polyalkylene glycol.

Most of the tetrapyrrole photosensitizers according to the present invention are administered through intravenous injection or drip infusion. On the other hand, the administration route of the ALAs according to the present invention is not limited to intravenous injection or drip infusion, and oral administration also including sublingual administration, transdermal administration using poultices or the like, and various other administration routes including administration using suppositories and intravesical injection are applicable to ALAs. Oral administration is advantageous in light of burdens on patients.

The dose of the ALAs is 30 mg to 3000 mg, preferably 500 mg to 2000 mg, in total of the ALAs per adult in terms of the amount of ALA hydrochloride.

The time interval from the administration of the photosensitizer or the ALAs according to the present invention to irradiation with infrared-spectrum light can be the same as that for usual visible light evaluation and is, for example, approximately 2 to 4 days from administration of the tetrapyrrole compound such as Photofrin or approximately 3 to 6 hours from administration of ALAs. By contrast, the time interval from the administration of the upconversion particle to light irradiation is not limited as long as the upconversion particle reaches a lesion before the light irradiation. In general, the upconversion particle administered directly or via a blood vessel rapidly reaches a lesion. In this case, the upconversion particle can be administered immediately before therapy. Since the upconversion particle is generally retained in the lesion such as cancer owing to the EPR effects, the particle may be administered a few days before therapy without problems. Alternatively, the therapy may be performed plural times with the particle retained while only the photosensitizer or the ALAs is further added.

In the case of PDT using the photodynamic therapeutic agent of the present invention, a lesion is irradiated with infrared-spectrum light when the photosensitizing substance and the upconversion particle are present in the lesion. As a result, the infrared-spectrum light having high permeability reaches the upconversion particle located even in the deep part of the body to emit visible light. The photosensitizing substance located in the vicinity of the upconversion particle is excited by the visible light to generate active oxygen so that the lesion can be treated. Under this mechanism, the therapy can be achieved in the deep part where excitation by visible light irradiation from outside is impossible due to the problem of the penetration depth of light. If a site to be treated is identified, the upconversion particle can be excited efficiently by infrared-spectrum light from many directions. For such a purpose, near-infrared light laser can be used advantageously.

If either the administered ALAs or, for example, the administered mannose-LNP complex or cancer antigen-specific antibody-LNP complex, or both, are selective for a lesion, the lesion and its neighborhood can be irradiated using infrared-spectrum light therapeutic apparatus or the like to thereby selectively treat the lesion.

None of currently known therapy methods are effective for, for example, cancer metastasis to the abdominal cavity, which is one of PDT targets. Nevertheless, this metastasis can be treated by the administration of the upconversion particle (e.g., LNP) and the photosensitizer or the ALAs and the subsequent irradiation with infrared-spectrum light for a long time. The problem of general PDT using visible light is a trouble caused by the light. Such a trouble caused by the light can be avoided by the PDT method according to the present invention because the upconversion particle is not directly excited by visible light.

Usual PDD using ALAs or photosensitizers involves absorbing irradiated blue visible light with high excitation efficiency through the Soret band of the photosensitizing substance and diagnosing the lesion on the basis of red fluorescence generated thereby. Since this technique is generally used in, for example, the diagnosis of the shallow part of the body or the determination of a site to be excised during surgery, even blue light with a low penetration depth seems to work fine. In actuality, fat tissues are often found in the surface layer of the lesion during surgery or the like. The blue visible light is absorbed by the fat and thus fails to excite the photosensitizing substance. The actual PDD of, for example, cancer metastasis to the sentinel lymph node, requires cutting the lesion after excision and observing the cut surface.

In the case of PDD using the photodynamic diagnostic agent of the present invention, red fluorescence is generated and can be observed sufficiently even from above the fat because the florescence can penetrate through the fat tissues. Since infrared-spectrum light is easily permeable to the fat, the upconversion particle (e.g., LNP) emits visible light. Furthermore, the photosensitizing substance emits long-wavelength fluorescence having high permeability. In this way, the presence or absence of metastasis can be obtained without excision. This will come as good news to QOL. In the case of a focus having a small amount of fat, even excitation by blue visible light can sufficiently produce fluorescence. The irradiated blue visible light, however, renders the focus blue to a considerable extent and therefore hinders the observation of normal tissues. By contrast, use of the infrared-spectrum light as excitation light does not hinder observation by any means because this light is invisible to human eyes.

Hereinafter, the present invention will be described in more detail with reference to Examples. However, the present invention is not limited by these Examples.

Example 1

[Generation of Singlet Oxygen Via Commercially Available LNP-(1)-]

The generation of singlet oxygen $^1O_2$ was detected using 1,3-diphenylisobenzofuran (DPBF).

100 ml of dimethyl sulfoxide (DMSO), 2.8 mg ($1 \times 10^{-4}$ M) of DPBF, and 2.0 mg ($2 \times 10^{-5}$ M) of PPIX were added to a beaker light-shielded with aluminum foil, and the mixture was stirred. A 25 ml aliquot thereof was transferred to another light-shielded vial. 250 mg of commercially available LNP ("Up-Conversion Anti-Counterfeit Phosphor (Green)" manufactured by Shanghai Keyan Phosphor Technology Co. Ltd.) was added to the vial, which was then irradiated from 50 mm above with 980-nm NIR (output: 400 mA) using semiconductor laser. 500 µl of a sample was collected at 0, 3, 5, 7, 10, 15, and 20 min (the start of irradiation is defined as 0 min) with stirring and transferred to a 1.5-ml Eppendorf tube, followed by centrifugation at 10000 rpm for 5 min. After the centrifugation, 40 µl of the supernatant was diluted 15-fold with 560 µl of DMSO. The absorbance was measured at 415 nm (LNP(+),NIR(+)). The remaining 75 ml of the sample was subjected to control experiments. Negative control experiments were conducted in the absence of NIR irradiation (LNP(+),NIR(−)) and in the absence of LNP (LNP(−),NIR(+)). Similarly, a positive control experiment was conducted under a condition involving irradiation with 400-nm UV known to be capable of exciting PPIX (UV(+),LNP(−)). The results are shown in FIG. 1.

As shown in FIG. 1, decrease in absorbance was observed under the NIR(+),LNP(+) and UV(+),LNP(−) conditions, showing that DPBF was decomposed. This suggested that singlet oxygen was generated. By contrast, such decrease in absorbance was not confirmed under the NIR(+),LNP(−) and NIR(−),LNP(+) conditions. These results demonstrated that NIR irradiation can indirectly excite PPIX via LNP to generate singlet oxygen.

Example 2

[Generation of Singlet Oxygen Via Commercially Available LNP-(2)-]

The generation of singlet oxygen $^1O_2$ was detected in the same way as in Example 1 using DPBF.

100 ml of dimethyl sulfoxide (DMSO), 2.8 mg ($1 \times 10^{-4}$ M) of DPBF, and 3.6 mg ($3.6 \times 10^{-5}$ M) of PPIX were added to a beaker light-shielded with aluminum foil, and the mixture was stirred. A 25 ml aliquot thereof was transferred to another light-shielded vial. 62.5 mg of commercially available LNP was added to the vial, which was then irradiated from 50 mm above with 980-nm NIR (output: 400 mA) using semiconductor laser. 500 µl of a sample was collected at 0, 1, 2, 3, 6, 8, 10, and 15 min (the start of irradiation is defined as 0 min) with stirring and transferred to a 1.5-ml Eppendorf tube, followed by centrifugation at 10000 rpm for 5 min. After the centrifugation, 40 µl of the supernatant was diluted 15-fold with 560 µl of DMSO. The absorbance was measured at 415 nm (LNP(+),NIR(+)). The remaining 75 ml of the sample was subjected to control experiments. Negative control experiments were similarly conducted in the absence of both NIR irradiation and LNP (LNP(−),NIR(−)), in the absence of NIR irradiation (LNP(+),NIR(−)), and in the absence of LNP (LNP(−),NIR(+)). The results are shown in FIG. 2.

As shown in FIG. 2, decrease in absorbance was observed under the NIR(+),LNP(+) condition, showing that DPBF was decomposed. This suggested that singlet oxygen was generated. By contrast, such decrease in absorbance was not confirmed under the NIR(−),LNP(−), NIR(+),LNP(−), and NIR(−),LNP(+) conditions. These results demonstrated that NIR irradiation can indirectly excite PPIX via LNP to generate singlet oxygen.

Example 3

[Test on Cytotoxicity of Commercially Available LNP]

Human gastric cancer-derived cell line MKN45 cells were cultured in the presence of LNP and subjected to a test on the cytotoxicity of commercially available LNP.

A medium in a 10-cm dish containing MKN45 cells cultured in a liquid medium (RPMI-1640, FBS(+), and PSN(+)) was aspirated, and the cells were washed with 3 ml of a PBS solution. 1 ml of trypsin was added thereto, and the mixture was incubated (37° C. and 5% $CO_2$) for 5 minutes. The enzymatic reaction of trypsin was terminated by the addition of 5 ml of a fresh medium. A total of 6 ml of the reaction mixture was centrifuged at 1100 rpm for 5 minutes. In this procedure, 10 µl of the sample was mixed with a dye trypan blue, which dyes dead cells. The number of live cells was counted using a hemacytometer. After the centrifugation, the supernatant was aspirated, and 2 ml of a fresh medium was added to the cells. The resulting cells were inoculated at a concentration of 100 µl/well ($2 \times 10^4$ cells/well) to a total of 48 wells of a 96-well plate to which 12 series involving ten 2-fold LNP dilution series starting at a concentration of 10 mg/ml, a control, and a blank were assigned (n=4). After overnight culture, the medium in each well was discarded, and the cells were washed with 100 µl of a PBS solution. 100 µl of a fresh medium and 10 µl of an MTT methanol solution diluted 10-fold with PBS were added to each well. After incubation for 4 hours, 10% SDS was added thereto at a concentration of 100 µl/well, and the mixture was incubated overnight. The absorbance was measured at 570 nm to 660 nm. The results are shown in FIG. 3.

As is evident from the graph of FIG. 3, cytotoxicity was confirmed in a manner dependent on the concentration of commercially available LNP. In response to this result, subsequent experiments were conducted at LNP concentrations of 2.0 to 2.5 mg/ml that did not influence viability.

Example 4

[ALA-PDT Using Commercially Available LNP-(1)-]

MKN45 cells were irradiated with NIR in the presence of ALA and LNP to confirm whether cell death occurred.

A medium in a 10-cm dish containing MKN45 cells cultured in a liquid medium (RPMI-1640, FBS(+), and PSN(+)) was aspirated, and the cells were washed with 3 ml of a PBS solution. 1 ml of trypsin was added thereto, and the mixture was incubated (37° C. and 5% $CO_2$) for 5 minutes. The enzymatic reaction of trypsin was terminated by the addition of 5 ml of a fresh medium. A total of 6 ml of the reaction mixture was centrifuged at 1100 rpm for 5 minutes. In this procedure, 10 µl of the sample was mixed with a dye trypan blue, which dyes dead cells. The number of cells was counted using a hemacytometer. After the centrifugation, the supernatant was aspirated, and 2 ml of a fresh medium was added to the cells. The resulting cells were inoculated at a concentration of 100 µl/well (2×10$^4$ cells/well) to a 96-well plate for ALA concentrations 1000, 100, 10, and 0 µM and a blank. LNP(+) and LNP(−) series were prepared per sample, and these samples were divided into two different plates for NIR(+) and NIR(−). After overnight culture, the medium in each well was discarded. 100 µl of a fresh medium (containing 2.5 mg/ml LNP for the LNP(+) series) and 0.2 M ALA adjusted to the concentrations mentioned above were added to each well of the plates. After incubation for 4 hours, each plate was irradiated from 50 mm above with 980-nm NIR (400 mA) for 3 min/well. After overnight culture, the medium in each well was discarded, and the cells were washed with 100 µl of a PBS solution. 100 µl of a fresh medium and 10 µl of an MTT methanol solution diluted 10-fold with PBS were added to each well. After incubation for 4 hours, 10% SDS was added thereto at a concentration of 100 µl/well, and the mixture was incubated overnight. The absorbance was measured at 570 nm to 660 nm. The results are shown in FIG. 4.

As is also evident from FIG. 4, no change was observed in cell viability under the condition involving no NIR irradiation, whereas slight reduction in viability was confirmed under the LNP(−),NIR(+) condition. This is probably because of heat generation, etc. These results demonstrated ALA-PDT activity brought about by the upconversion luminescence of commercially available LNP under NIR irradiation. Approximately 40% cells, however, still survived. Thus, the culture time after addition of ALA should be extended from 4 hours to 24 hours for the larger accumulation of PPIX in order to achieve lower viability.

Example 5

[ALA-PDT Using Commercially Available LNP-(2)-]

ALA-PDT was performed using commercially available LNP in the same way as in Example 4 except that the concentration of MKN45 cells was changed to 2×10$^4$ cells/well; the ALA concentrations were changed to 2000, 1000, 100, 10, and 0 µM; the culture time after addition of ALA was changed from 4 hours to 24 hours; and the NIR irradiation time was changed to 90 min/well. The results are shown in FIG. 5.

As is also evident from FIG. 5, no change was confirmed in cell viability under the condition involving no NIR irradiation and under the LNP(−),NIR(+) condition. By contrast, the viability was drastically reduced under the NIR(+),LNP(+) condition, demonstrating ALA-PDT activity brought about by the upconversion luminescence of commercially available LNP under NIR irradiation.

Example 6

[Synthesis of Mannose-LNP Complex]

Oleic acid (OA)-coated LNP (NaYF$_4$; Yb/Er or Tm/Gd=18/2/30 mol %) was synthesized.

1.2 g of NaGH, 20 ml of ethanol, 20 ml of oleic acid, 8 ml of 0.2 M RECl$_3$ (8 ml of H$_2$O, 244.7 mg of YCl$_3$.6H$_2$O, 112.6 mg of YbCl$_3$.6H$_2$O, 12.2 mg of ErCl$_3$.6H$_2$O or TmCl$_3$.6H$_2$O, and 114.5 mg of GdCl$_3$.xH$_2$O), and 4 ml of 2 M NH$_4$F (4 ml of H$_2$O and 298 mg of NH$_4$F) were added to 6 ml of H$_2$O, and the mixture was reacted with stirring at 1400 rpm at 200° C. for 2 hours in an autoclave. The reaction mixture was cooled to room temperature for approximately 2 hours and centrifuged at 10000 rpm for 10 minutes. The supernatant was discarded, and the pellet was washed three times with each of H$_2$O and EtOH.

Olefin in the oleic acid site of the oleic acid-coated LNP was oxidatively cleaved.

200 mg of the OA-coated LNP (NaYF$_4$; Yb/Er or Tm/Gd=18/2/30 mol %) thus synthesized, 140 ml of tert-butanol, 20 ml of H$_2$O, and 10 ml of 5 wt % K$_2$CO$_3$(aq) were added to 200 ml of cyclohexane, and the mixture was stirred at room temperature. 20 minutes later, 40 ml of a Lemieux-von Rudloff reagent (40 ml of H$_2$O, 36.8 mg of KMnO$_4$, and 900.5 mg of NaIO$_4$) was added thereto, and the mixture was reacted in an oil bath at 40° C. for 48 hours. The resulting reaction mixture was centrifuged at 10000 rpm for 10 minutes and washed with H$_2$O, acetone, and EtOH. After the washing, 100 ml of HCl (adjusted in advance to pH 4 to 5) was added thereto, and the mixture was stirred at room temperature for 30 minutes. Then, the reaction solution was centrifuged at 10000 rpm for 10 minutes and washed twice with H$_2$O.

NEtMan was added to the oxidized oleic acid-coated LNP.

70 mg of the thus-synthesized LNP (NaYF$_4$; Yb/Er/Gd=18/2/30 mol %) having the oxidized oleic acid site was dissolved in 10 ml of H$_2$O. 700 mg of each of NHS and EDC was dissolved in 10 ml of H$_2$O. These solutions were stirred at room temperature. 20 minutes later, a solution containing 500 mg of NEtMan dissolved in 10 ml of H$_2$O was added thereto, and the mixture was reacted at room temperature for 4 hours. 10 ml of amino ethanol was added thereto, and the mixture was further reacted for 4 hours. The resulting reaction solution was centrifuged at 10000 rpm for 10 minutes to recover LNP. The recovered LNP was washed with H$_2$O.

Example 7

[Generation of Singlet Oxygen Via Synthetic LNP]

An experiment was conducted on the generation of singlet oxygen via synthetic LNP in the same way as in Example 2 except that the oleic acid-coated LNP prepared in Example 6 was used instead of commercially available LNP. The results are shown in FIG. 6.

Figure 6:
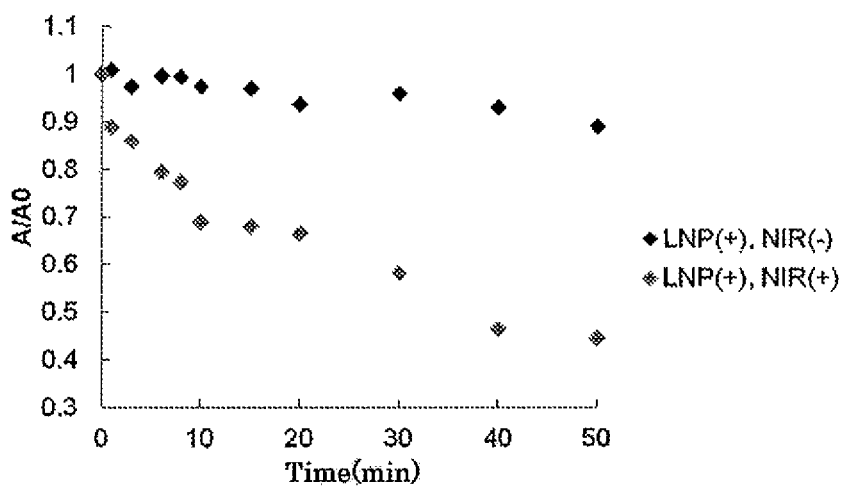
FIG. 6 is a diagram showing results of an experiment on the generation of singlet oxygen from protoporphyrin IX by the emission of synthetic lanthanide particles.

As shown in FIG. 6, decrease in absorbance was observed under the NIR(+),LNP(+) condition, showing that DPBF was decomposed. This suggested that singlet oxygen was generated. By contrast, such decrease in absorbance was not confirmed under the NIR(−),LNP(+) condition. These results demonstrated that NIR irradiation can indirectly excite PPIX via synthetic LNP to generate singlet oxygen.

Example 8

[Test on Cytotoxicity of Synthetic LNP]

A cytotoxicity test was conducted in the same way as in Example 3 except that the synthetic LNP prepared in Example 6 and commercially available LNP were used. The results are shown in FIG. 7.

Figure 7:
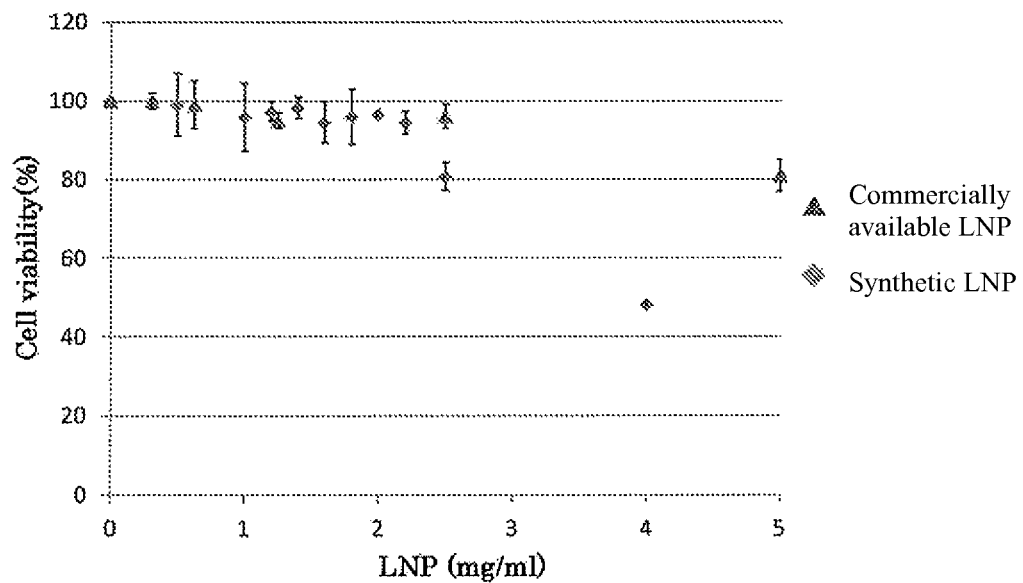
FIG. 7 is a diagram showing results of a test on the cytotoxicity of synthetic lanthanide particles.

As is evident from the graph of FIG. 7, cytotoxicity was confirmed for both the synthetic and commercially available products in a manner dependent on the concentration of LNP. The synthetic LNP was shown to have higher cytotoxicity than that of the commercially available LNP.

Example 9

[ALA-PDT Using Synthetic LNP-(1)-]

ALA-PDT was performed using synthetic LNP in the same way as in Example 5 except that: the concentration of the synthetic LNP prepared in Example 6 was set to 2 mg/mL; and the ALA concentrations were changed to 2000, 1500, 1000, 100, and 0 μM. The results are shown in FIG. 8.

Figure 8:
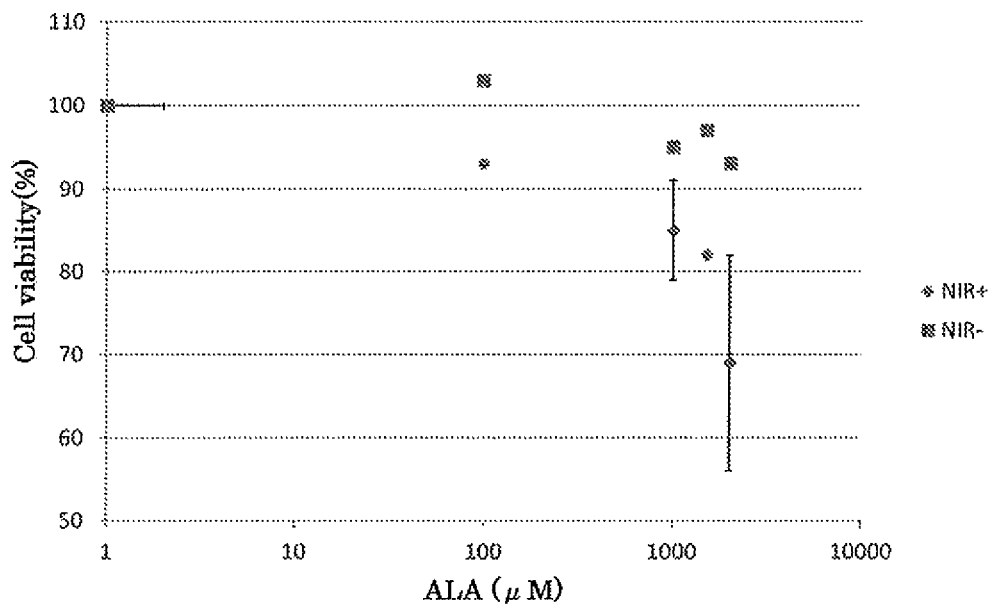
FIG. 8 is a diagram showing results of an experiment on cancer cell injury by the emission of synthetic lanthanide particles and protoporphyrin IX.

As is also evident from FIG. 8, no change was confirmed in cell viability under the condition involving no NIR irradiation (NIR(−),LNP(+) condition). By contrast, the viability was drastically reduced under the NIR(+),LNP(+) condition, demonstrating ALA-PDT activity brought about by the upconversion luminescence of synthetic LNP under NIR irradiation.

INDUSTRIAL APPLICABILITY

The photodynamic therapeutic or diagnostic agent of the present invention attains a deep body penetration, is optimal for PDT or PDD, and can be used advantageously in, for example, the therapy of various cancers (e.g., lung cancer, gastric cancer, uterine cancer, and skin cancer) or various infectious diseases.

The invention claimed is:

1. A photodynamic therapeutic or diagnostic agent comprising: a lanthanide particle having a particle size of 50 nm to 200 nm, that emits upconversion luminescence by infrared-spectrum light; and a compound represented by the following formula (I):

$$R^2R^1NCH_2COCH_2CH_2COR^3 \quad (I)$$

wherein $R^1$ and $R^2$ each independently represent a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group, or a salt thereof, wherein the lanthanide particle forms a complex with mannose, wherein the mannose is directly attached to the lanthanide particle via a carboxyl and/or amide moiety.

2. The photodynamic therapeutic or diagnostic agent according to claim 1, wherein the infrared-spectrum light is near-infrared light having a wavelength of 0.7 μm to 2.5 μm.

3. The photodynamic therapeutic or diagnostic agent according to claim 1, wherein the photodynamic therapeutic or diagnostic agent is a therapeutic or diagnostic for cancer.

4. The photodynamic therapeutic or diagnostic agent according to claim 2, wherein the photodynamic therapeutic or diagnostic agent is a therapeutic or diagnostic for cancer.

5. The photodynamic therapeutic or diagnostic agent according to claim 1, wherein the lanthanide particle is a lanthanide nanoparticle (LNP).

6. The photodynamic therapeutic or diagnostic agent according to claim 5, wherein the mannose-LNP complex comprises 1-aminoethylmannose.

7. The photodynamic therapeutic or diagnostic agent according to claim 5, wherein the mannose is directly attached an LNP that is coated with oxidized oleic acid.

* * * * *